United States Patent [19]

Berne et al.

[11] 4,364,922

[45] Dec. 21, 1982

[54] ADENOSINE ANTAGONISTS IN THE TREATMENT AND DIAGNOSIS OF A-V NODE CONDUCTION DISTURBANCES

[75] Inventors: Robert M. Berne; Luiz Belardinelli; Rafael Rubio, all of Charlottesville, Va.

[73] Assignee: University of Virginia Alumni Patents Foundation, Charlottesville, Va.

[21] Appl. No.: 196,652

[22] Filed: Oct. 14, 1980

[51] Int. Cl.$^3$ ................ A61K 49/00; A61K 31/52; A61K 31/46
[52] U.S. Cl. ............................ 424/9; 424/253; 424/265
[58] Field of Search .................... 424/9, 253, 265

[56] References Cited

U.S. PATENT DOCUMENTS

| | | | |
|---|---|---|---|
| 3,317,533 | 5/1967 | DeRidder | 424/253 X |
| 3,493,573 | 2/1970 | Joullie | 424/253 X |
| 3,928,609 | 12/1975 | Behrakis | 424/253 |
| 3,962,243 | 7/1976 | Roldan | 424/253 X |
| 3,989,833 | 11/1976 | Jonas | 424/253 X |
| 4,117,132 | 9/1978 | Seebach | 424/253 |
| 4,144,340 | 3/1979 | Offermanns | 424/253 |
| 4,153,696 | 5/1979 | Kleeman | 424/253 |

OTHER PUBLICATIONS

Afonso, *J. Physiol.*, vol. 241, 1974, pp. 299–308.
Berne, *American Journal of Physiology*, vol. 204, pp. 317–322 (1963).
Rubio et al., *Journal of Molecular and Cellular Cardiology*, vol. 6, pp. 561–566 (1974).
Bunag et al., *Circulation Research*, vol. XV, pp. 83–88 (1964).
Katori et al., *Circulation Research*, vol. XIX, pp. 420–425 (1966).
Rubio et al., *American Journal of Physiology*, vol. 216, pp. 56–62 (1969).
Rubio et al., *Circulation Research*, vol. XXV, pp. 407–415 (1969).
Curnish et al., *Proceedings of the Society for Experimental Biology and Medicine*, vol. 141, pp. 593–598 (1972).
Wiedmeier et al., *American Journal of Physiology*, vol. 223, pp. 51–54 (1972).
Berne et al., "Challenges to the Adenosine Hypothesis for the Regulation of Coronary Blood Flow," in *Current Topics in Coronary Research*, Bloor and Olsson, editors, Plenem Publishing Corp., N.Y., pp. 3–10 (1973).
Rubio et al., *American Journal of Physiology*, vol. 225, pp. 938–953 (1973).
Thomas et al., *Journal of Molecular and Cellular Cardiology*, vol. 7, pp. 115–123 (1975).
Mustafa et al., *American Journal of Physiology*, vol. 228, pp. 1474–1478 (1975).
Foley et al., *Journal of Molecular and Cellular Cardiology*, vol. 10, pp. 293–300 (1978).
Foley et al., *American Journal of Physiology*, vol. 236, pp. H833–H838 (1979).
Watkinson et al., *American Journal of Physiology*, vol. 236, pp. H13–H21 (1979).
Jacob et al., *American Journal of Physiology*, vol. 198, pp. 322–326 (1960).
Jacob et al., *Proceedings of the Society for Experimental Biology and Medicine*, vol. 107, pp. unknown (1961).
Miller et al., *Circulation Research*, vol. 45, pp. 708–718 (1979).
Berne et al., *Circulation Research*, vol. 35, pp. 262–271 (1974).
Rubio et al., *American Journal of Physiology*, vol. 228, pp. 1896–1902 (1975).
Winn et al., *Circulation Research*, vol. 45, pp. 486–492 (1979).
Berne et al., "Mechanism of Adenosine Incorporation into Brain," source unavailable.
Winn et al., "Brain Adenosine Production During the Initial 60 Seconds of Bicuculline Seizures in Rats," source unavailable.
Winn et al., "Changes in Adenosine During Sustained Hypoxia," source unavailable.
Dobson et al., *Circulation Research*, vol. XXIV, pp. 375–384 (1971).
Bockman, et al., *Pflugers Arch*, vol. 355, pp. 229–241 (1975).
Bockman et al., *American Journal of Physiology*, vol. 230, pp. 1531–1537 (1976).
Schraeder et al., *Journal of Molecular and Cellular Cardiology*, vol. 7, pp. 427–433 (1975).

Imai et al., *Circulation Research*, vol. XV, pp. 443–450 (1964).
Belardinelli et al., *Pflugers Arch.*, vol. 380, pp. 19–27 (1979).
Berne et al., "Effect of Adenosine on Contraction of Vascular Smooth Muscle," in *Ionoic Actions on Vascular Smooth Muscle*, Betz, editor, Springer-Verlag, Berlin, pp. 137–140 (1976).
Herlihy, et al., *American Journal of Physiology*, vol. 230, pp. 1239–1243 (1976).
Harder et al., *Circulation Research*, vol. 44, pp. 176–172 (1979).
Schraeder et al., *American Journal of Physiology*, vol. 223, pp. 159–166 (1972).
Berne et al., "Response of Large and Small Coronary Arteries to Adenosine, Nitroglycerine, Cardiac Glycosides, and Calcium Antagonists," source unavailable.
Berne, *Physiological Reviews*, vol. 44, pp. 1–29 (1964).
Berne et al., *American Journal of Cardiology*, vol. 24, pp. 776–781 (1969).
Berne et al., *Circulation, Supp.* IV to vols. XXXIX and XL, pp. IV-240–IV-251 (1969).
Berne et al., *Advances in Cardiology*, vol. 5, pp. 56–66 (1970).
Berne et al., *Circulation Research, Supp.* I to vols. XXVII and XXIX, pp. I-115–I-119 (1971).
Berne et al., *Circulation Research, Supp.* III to vols. 34 and 35, pp. III-109–III-120 (1974).
Miller et al., *Circulation Research*, pp. 390–397 (1978).
Berne et al., *American Journal of Physiology*, vol. 229, pp. 1625–1631 (1975).
Jageneau et al., *Naunyn–Schmiedebergs Arch. Pharmak.*, vol. 256, pp. 16–23 (1969).
Stafford, *British Journal of Pharmacology and Chemotherapy*, vol. 28, pp. 218–226 (1966).
Afonso et al., *Circulation Research*, vol. XXII, pp. 43–48 (1968).
Bittar et al., *Pharmacological Research Communications*, vol. 2, pp. 231–242 (1970).
Nott, *British Journal of Pharmacology*, vol. 39, pp. 287–295 (1970).
Afonso, *Circulation Research*, vol. XXVI, pp. 743–752.
Kubler et al., *Journal of Molecular and Cellular Cardiology*, vol. 1, pp. 23–38 (1970).
Miura et al., "Potentiation of Reactive Hyperemia in the Coronary and Femoral Circulation by the Selective Use of 2,6-Bis(Diethanolamino)-4,8-dipiperidinopyrimidol[5,4-d]pyrimidine," source unavailable.
Olsson et al., *Circulation Research*, vol. 39, pp. 93–98 (1976).
Olsson et al., *Federation Proceedings*, vol. 37, pp. 418 (1978).
Olsson et al., *Life Sciences*, vol. 21, pp. 1343–1350 (1977).
Schrader et al., *Pflugers Arch*, vol. 369, pp. 251–257 (1977).
Drury et al., *Journal of Physiology (London)*, vol. 68, pp. 214–237 (1929).
Cook et al., *Circulation Research*, vol. VI, pp. 735–739 (1958).
Buckley et al., *Circulation Research*, vol. IX, pp. 242–249 (1961).
Richman et al., *American Journal of Physiology*, vol. 207, pp. 1139–1142 (1964).
Olsson et al., *American Journal of Physiology*, vol. 208, pp. 231–236 (1965).
Olsson, *Circulation Research*, vol. XXVI, pp. 301–306 (1970).
Olsson et al., *Circulation Research*, vol. XXXI, pp. 767–778 (1972).
Schrader et al., *Pflugers Arch*, vol. 369, pp. 1–6 (1977).
Schrader et al., *Pflugers Arch*, vol. 372, pp. 29–35. (1977).
Olsson et al., *Circulation Research*, vol. 42, pp. 358–362 (1978).
Schnaar et al., *American Journal of Physiology*, vol. 223, pp. 223–228 (1972).
de Gubareff et al., *Journal of Pharmacology and Experimental Therapeutics*, vol. 148, pp. 202–214 (1965).
Bittar et al., *American Journal of Physiology*, vol. 220, pp. 812–815 (1971).
Afonso et al., *Journal of Physiology (London)*, vol. 221, pp. 589–599 (1972).
Bunger et al., *Pflugers Arch*, vol. 358, pp. 213–224 (1975).
Merrill et al., *Circulation Research*, vol. 42, pp. 225–229 (1978).
Giles et al., *Cardiovascular Research*, vol. 11, pp. 113–121 (1977).
Afonso et al., *Basic Research in Cardiology*, vol. 70, pp. 390–400 (1975).

Mitenko et al., *New England Journal of Medicine*, vol. 289, pp. 600–603 (1973).
Adgey et al., *Lancet*, pp. 1097–1101 (1968).
Tans et al., "A-V Nodal Block In Acute Myocardial Infarction," source not available.

*Primary Examiner*—Anna P. Fagelson
*Attorney, Agent, or Firm*—Oblon, Fisher, Spivak, McClelland & Maier

[57] ABSTRACT

A method of relieving atrioventricular conduction block by administering to a human or animal an effective amount of an adenosine antagonist that competitively inhibits adenosine or that reduces the level of adenosine present in myocardial tissue and associated fluids. A method of diagnosing atrioventricular conduction block caused by ischemia of the heart by measuring the time delay between atrial and ventricular excitation before and after the administration of an adenosine antagonist. Specific antagonists disclosed include methylxanthines.

27 Claims, 15 Drawing Figures

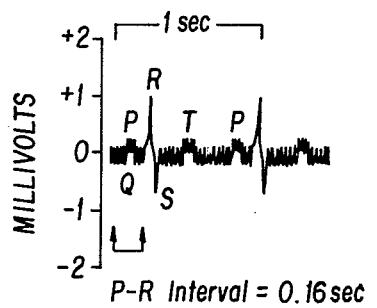
NORMAL ELECTROCARDIOGRAM
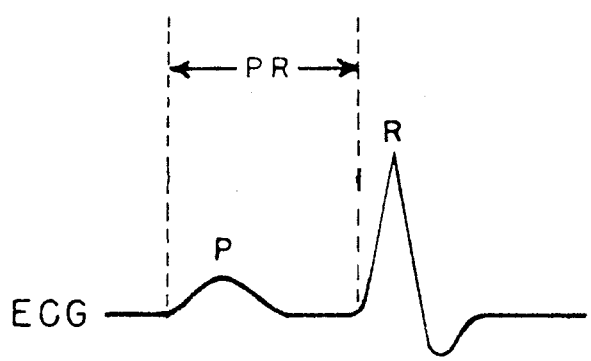
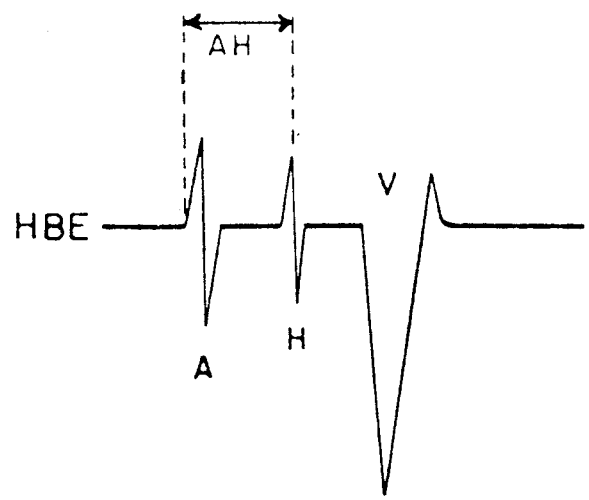
FIG. 1

FIG. 5 EFFECT OF ADENOSINE ON A-V CONDUCTION IN RABBIT HEART

FIG. 8
P-P = 840 msec
*P-R = 310 msec
H.R. = 71 bpm
CONTROL
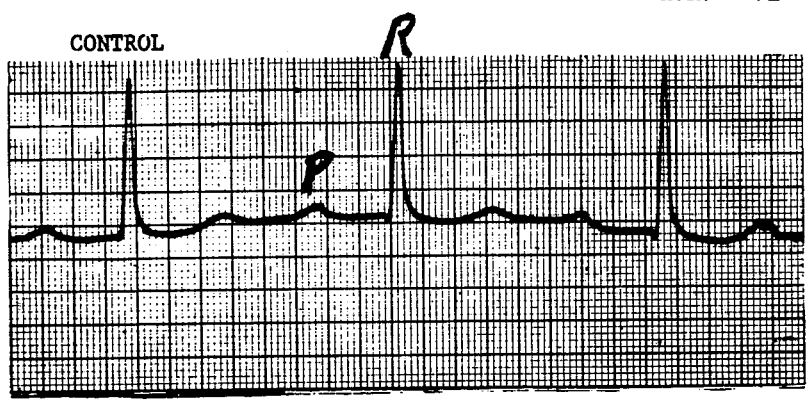
P-P = 835 msec
*P-R = 240 msec
H.R. = 72 bpm
10 Min. AMINOPHYLLINE, I.V. 3mg/Kg
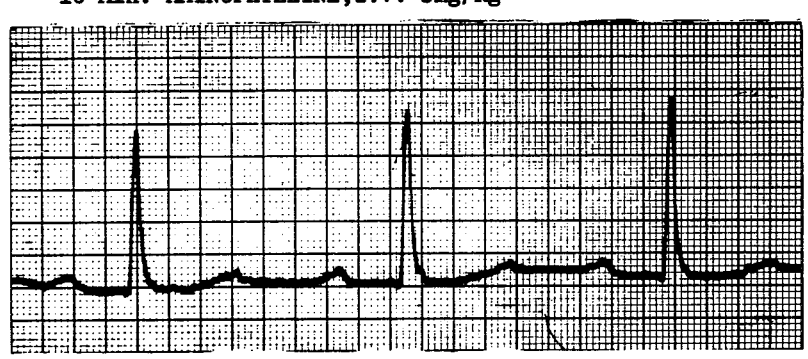
P-P = 820 msec
*P-R = 280 msec
H.R. = 73 bpm
2 Hrs. AMINOPHYLLINE
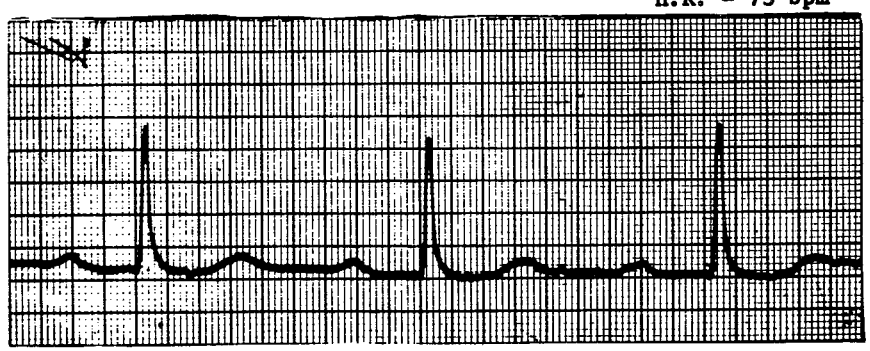

PATIENT ( R.G.)
CONTROL                           2nd DEGREE A-V BLOCK
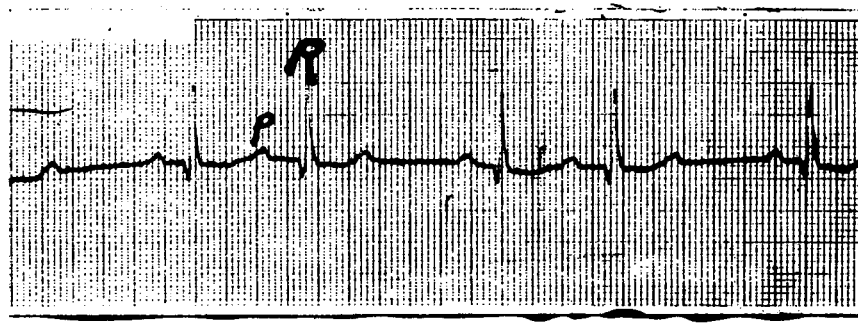
15 Min. AMINOPHYLLINE (3mg/Kg, I.V.)
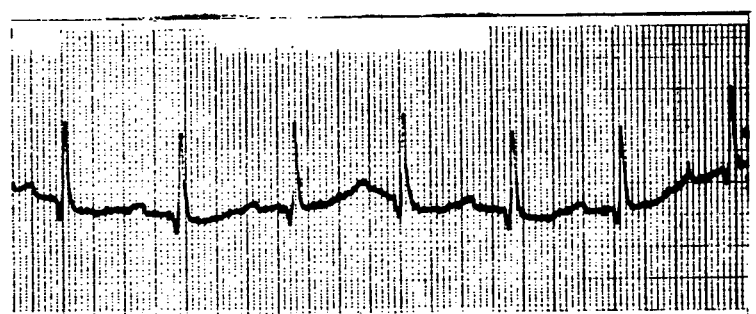
2 Hrs. AMINOPHYLLINE
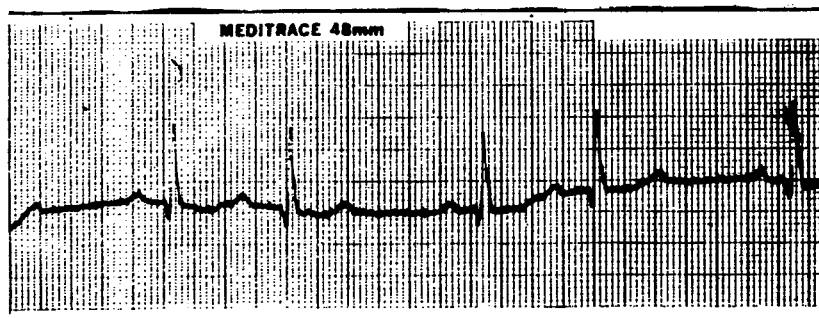
FIG. 9

ADENOSINE ANTAGONISTS IN THE TREATMENT AND DIAGNOSIS OF A-V NODE CONDUCTION DISTURBANCES

BACKGROUND OF THE INVENTION

1. Field of the Invention

The present invention relates to methods for diagnosis and treatment of atrioventricular conduction blockage.

2. Description of the Prior Art

Proper functioning of the pathway through which impulses that govern the heart beat are transmitted is vital for any organism. In the mammalian heart the electrical component of each heart beat originates in the sinoatrial node (pacemaker) of the heart and must pass through the atrioventricular (A-V) node in order to reach the ventricles and elicit the contraction needed to pump blood.

The electrical components of a heart beat can be detected by an electrocardiogram (EKG) and appear as follows: first, an electrical impulse known as P-wave, which indicates the triggering of the sinoatrial node and activation of the atria, and second, a complex group of electrical impulses individually named Q-, R-, S-, and T-waves and collectively known as the ventricular complex, which indicates that the signal has passed the A-V node and that the ventricles are activated to contract. The Q-wave is sometime quite small and may not be visible; therefore, the interval between atrial and ventricular depolarization (Activation) is generally measured by the P-R interval. An EKG of a normal heart is shown in FIG. 1. Normally, both the interval between two P-waves (the time of a complete heart beat) and the interval between a P-wave and following R-wave are consistent from one heart beat to another. The normal R-R interval is about 0.2 second. However, when the transmission of a signal through the A-V node is impaired, there is an increase in the time delay from the P-wave to the R-wave. This can be seen in FIG. 8. Impaired functioning of the heart indicated by an increase in the P-R interval is known as first degree heart block. With increased impairment of A-V conduction, the time delay between the P-wave and the R-wave becomes longer. Eventually, the signal may fail to be transmitted at all, and some of the expected contractions of the ventricles will not occur, resulting in the condition known as second degree heart block. For example this condition occur when there are two atrial beats for each ventricular beat, known as 2:1 A-V block. Other relationship between beats in second degree heart block, such as 3:2 A-V block, are also possible, as shown in FIG. 9. If no A-V conduction occurs at all, the beating of the atria and ventricles becomes completely dissociated, and the ventricles beat at a much slower rate than normal, resulting in severely decreased efficiency of the heart as a pump. This dissociation is known as third degree heart block. Continued functioning of the heart in this mode may result in imminent death.

Several conditions of the heart are known to affect A-V node transmission. These includes ischemia (low blood flow to heart tissue) and hypoxia (low oxygen blood level) of the A-V node. Disorders that can cause hypoxia and ischemia include partial or complete obstruction of arteries leading to the heart and constriction of such arteries. Furthermore, it has been known that A-V node action potentials (electrical potential during activity of the node) are depressed by hypoxia and, concomitantly, the atria-to-His bundle conduction time is markedly increased. The His bundle is a small band of atypical cardiac muscle fibers that propagates the electrical signal from the atrial to the ventricular end of the A-V node. Additionally, stimulation of the vagus nerve, the parasympathetic nerve that controls heart beat, results in slowing of the heart beat and an increase in the P-R interval. The vagus nerve interacts with the heart by releasing acetylcholine, and, therefore, the presence of high levels of acetylcholine will also cause A-V conduction disturbances. Lastly, as easily as 1929 it was observed that adenosine, if injected in large amounts, can produce heart block. Adenosine is normally present in myocardial tissue, as well as in other tissues, but is normally present only in much lower concentrations than those that produce heart block. Adenosine and adenine nucleotides have been shown to produce dose-dependent A-V conduction block in guinea pig hearts. Adenosine is also known to depress $Ca^{2+}$-mediated action potentials in mammalian atria.

Presently, A-V node conduction blockage can be determined with certainty only from an electrocardiogram (EKG). If an EKG is not available, clinical techniques of heart beat monitoring by stethoscope or by taking of the pulse may give some indication of A-V node blockage, but with considerably less certainty.

Treatment of A-V conduction blockage is presently limited to administration of atropine and pacemakers. Atropine blocks the parasympathetic affect of the vagus nerve on the heart. Therefore, atropine is effective in treating A-V block caused by disorders of the vagus nerve. However, administration of atropine has not been effective in relieving A-V block in all cases for reasons that have previously been unknown. As shown in a 1968 clinical study only 10 of 20 patients with A-V block (second degree or complete), treated with atropine within 8 hours of the onset of symptoms of myocardial infarction, showed improved A-V conduction. No improvement was seen in the remaining 10 patients. Also, only 1 of 11 patients treated more than 8 hours after the onset of symptoms showed a favorable response to atropine. (Adgey et al, Lancet, 2, pp. 1097–1101 (1968)). Indeed, the administration of atropine in some instances has been observed to aggravate A-V node block.

Prior to investigations of one of the present inventors in the 1960's, there was no recognition that ischemia and hypoxia of the heart led to increased adenosine production in myocardial tissues. It was not until the three-way cause-and-effect relationship of hypoxia, adenosine production, and A-V node disturbance was recognized in the present invention that a rational treatment of A-V node conduction disturbances became possible. This novel treatment comprises the use of an adenosine antagonist to block the action of adenosine on the A-V node.

One class of adenosine antagonists, the group of compounds known as methylxanthines, are well known as reagents which relieve bronchial asthma. Methylxanthines are known to affect the heart but have not been used in cases of A-V node disturbances. In fact, many of the prior uses of methylxanthines in clinical situations are now contraindicated in conditions of hypoxia and ischemia. Methylxanthines are well known as stimulators of myocardial contraction (U.S. Pat. No. 3,928,609) and as dilators of coronary blood vessels (U.S. Pat. Nos.

4,153,696 and 3,989,833). Well known examples of methylxanthine are caffeine, which is 1,3,7-trimethylxanthine, and theophylline, which is 1,3-dimethylxanthine. The best known, clinically-used methylxanthine is aminophylline, the ethylenediamine derivative of theophylline. Several derivatives of theophylline have been proposed to be useful in treatment of tacharrhythmia (rapid heart beat; U.S. Pat. No. 4,144,340) and other unspecified arrhythmias (U.S. Pat. Nos. 3,962,243). These and other derivatives of theophylline act by releasing theophylline itself into the blood stream where they undergo hydrolysis (U.S. Pat. No. 4,085,214). However, past studies have shown that when theophylline was used to treat angina pectoris, the treatment resulted in increased heart rate and increased myocardial oxygen consumption (U.S. Pat. No. 3,896,127). In summary, methylxanthines have been used to stimulate heart contraction but in the process increase oxygen consumption, a condition that has detracted away from the use of methylxanthines in the treatment of conditions that may involve an ischemic heart.

SUMMARY OF THE INVENTION

It is therefore an objective of the invention to provide a method for the treatment of atrioventricular conduction block.

It is an additional objective of the invention to provide a selective diagnostic test for the determination of the cause of atrioventricular conduction block, thereby allowing rational treatment.

It is a further objective of the invention to provide a method for preventing the occurance of A-V conduction block in patients known to have ischemic or hypoxic heart conditions.

These and other objectives of the invention which will hereinafter become more readily apparent have been attained by providing a method of relieving atrioventricular conduction block comprising the step of administering to a human or animals an amount of an adenosine antagonist sufficient to alleviate atrioventricular conduction block, wherein said antagonist competitively inhibits adenosine or reduces the level of adenosine present in myocardial tissue and associated fluids.

DESCRIPTION OF THE PREFERRED EMBODIMENTS

Figure 2:
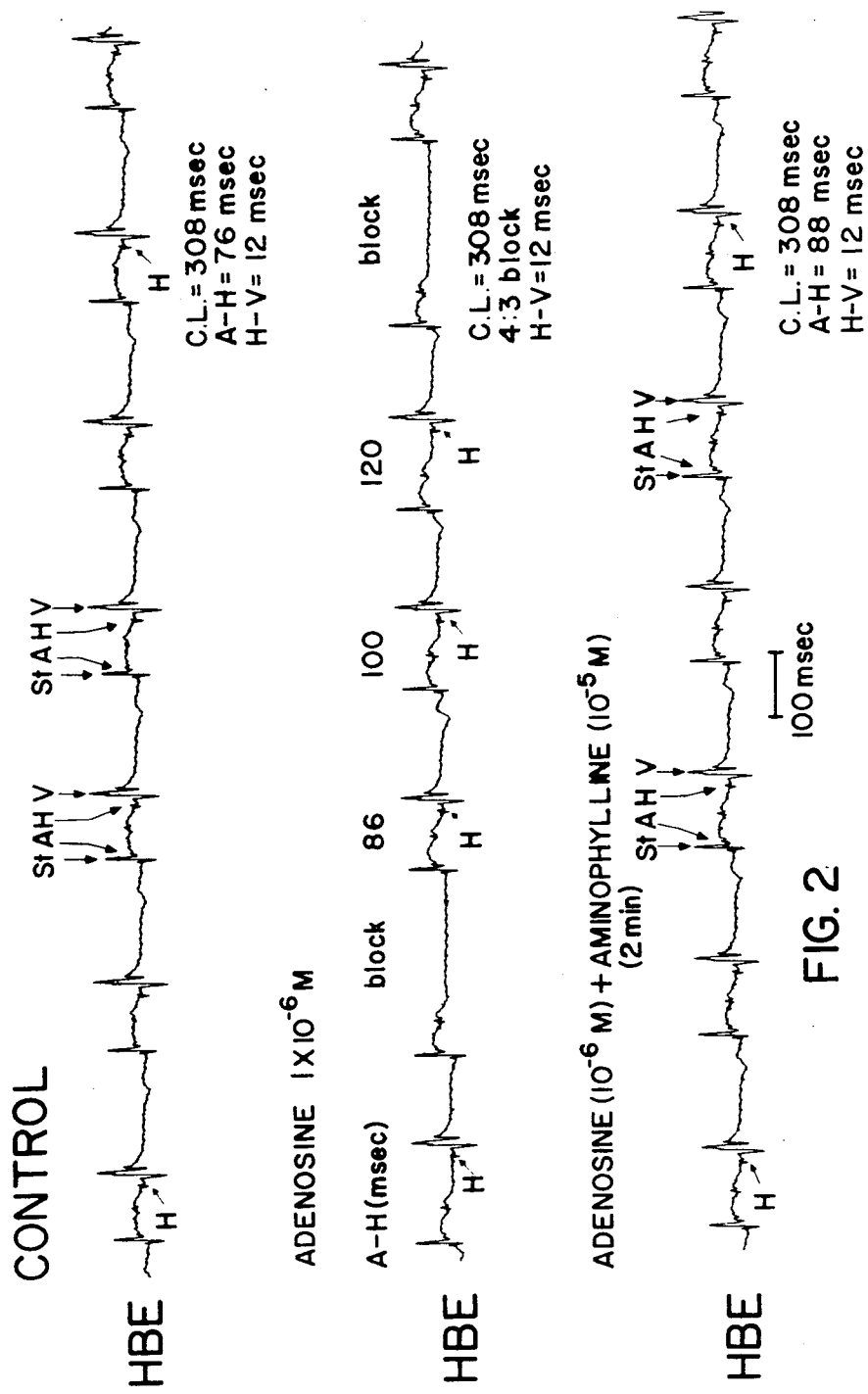

The present invention has succeeded in providing a diagnostic test for and a method of treatment of A-V node conduction disturbances. The present inventors have discovered that in response to hypoxia or ischemia, myocardial cells produce an excess of adenosine. This amount of adenosine is far greater than that which is present normally in myocardial tissue. The excess adenosine alters the performance of the heart muscle and blood vessels in the heart. In particular, the excessive amount of adenosine released from ischemic cells impairs A-V node conduction. Thus, the adenosine so produced is capable of interrupting the passage of the electrical impulse from the atria to the ventricles, which could lead to a slowing of heart rate and possible pump failure. The inventors have shown that impairment of A-V node function by hypoxia or ischemia can be reversed or prevented by administration of antagonists of adenosine. By an antagonist is meant an agent that acts, by whatever mechanism to reduce the effect of adenosine in myocardial tissue. An antagonist of adenosine may be a competitive inhibitor or a substance that reduces the concentration of adenosine by destroying adenosine or that causes its destruction by altering metabolic pathways normally present in cells or intercellular fluid. An irreversable inhibitor is not suitable for the present invention since the action of adenosine in performing its inherent regulatory functions must not be permanently impaired. Examples of known antagonists of adenosine are methylxanthines, which acts as competitive inhibitors, and adenosine deaminase or other enzymes, which effect the metabolism of adenosine in the body and reduce the level of adenosine present in myocardial tissue.

Methylxanthines are the antagonists that have been used in the clinical tests disclosed herein to alleviate A-V conduction block. The choice of methylxanthines should not be considered limiting since any antagonist of adenosine will alleviate A-V conduction block of the heart caused by excess adenosine, if the antagonist is properly administered.

Methylxanthine that have been approved for clinical use include
theophylline,
aminophylline,
dihydroxypropyl theophylline, and
theophylline calcium sulfate.

Methylxanthines that have recently been synthesized and which are suggested as being suitable for therapeutic use include
1-(hex-5-enyl)-3,7-dimethylxanthine,
1-(4-hydroxypentyl)-3,7-dimethylxanthine,
1-(2-ethyl-3-oxobutyl)-3,7-dimethylxanthine,
2-(7'-theophyllinemethyl)-1,3-dioxolane,
7-(2-(3,4-dihydroxyphenyl)-ethylamino)-ethyl)theophylline,
7-(3-(3-indolyl-(4)-oxy-2-hydroxypropylamino))propyl-theophylline,
1,3-dimethyl-8-(n-propyl)xanthine,
methyl 1,3-dimethyl-8-(cyclobutyl)xanthine-7-carboxylate,
1,8-dimethyl-3-(2-methyl-1-butyl)xanthine,
7-(3-phenylpropenyl)theophylline,
8-(2-(4-(m-chlorophenyl)piperazin-1-yl)-ethyl)-1,3-dimethyl-6,7-dihydro-8-H-imidazol[2,1-f]purine-2,4(1H,3H)dione
and similar compounds, these compounds listed here being a small selection of such methylxanthines. A more complete description of pro-drug forms of methylxanthines which release a methylxanthine in blood is provided in U.S. Pat. No. 4,061,753, issued Oct. 6, 1977, which is hereby incorporated by reference.

Clinical observations have confirmed the efficacy of methylxanthines in treating A-V conduction disturbances in patients with myocardial infarction. Knowledge that excess adenosine is responsible for the A-V node malfunction during hypoxia and ischemia has led to a method using methylxanthine to treat such conduction disturbances in patients. This treatment is based on the discovery of the cyclic nature of impaired blood supply and adenosine production. Impaired blood supply to myocardial tissue results in adenosine production by the myocardial tissue affected. This excess adenosine leads to A-V node block which causes ventricular slowing or arrest. This impairment of heart pumping leads to further impairment of blood supply, completing the cycle and resulting in more adenosine production and even more likelihood of complete heart failure. Therapy comprises the use of an antagonist of adenosine to break the cycle by counteracting the effects of excess adenosine.

In addition to their use as therapeutic agents, antagonists of adenosine can be used in diagnosis of A-V conduction disturbances. Administration of an effective amount of adenosine antagonist to a human patient or to animals exhibiting symptoms of A-V conduction block will enable determination of the cause of the block. Organisms that respond to the administration of an adenosine antagonist can be diagnosed as suffering from hypoxia or ischemia and can be treated with an adenosine antagonist to relieve the block or to prevent the recurrance of the block. Organisms having A-V conduction block caused by other factors, such as a disturbance of the vagus nerve, digitalis intoxication, or an infarct of the conduction pathway, will not respond to the administration of an adenosine antagonist, and may be rationally treated by other techniques.

This invention is also not concerned with disorders such as atrial fibrillation, ventricular fibrillation, arrythmias not caused by adenosine, heart failure, cardiac arrest, coronary artery disease, valvular complications, pulmonary edema, high blood pressure, and other disorders not caused by adenosine. Likewise this invention is not concerned with those disorders that are properly treated with epinephrine or norepinephrine or their derivatives, since these materials stimulate the heart and increase oxygen consumption to the detriment of an ischemic or hypoxic heart. Nor is this a treatment for angina pectoris, since there is often no pain present with A-V block. However, any of these disturbances may be present at the same time as A-V block.

Dosages of theophylline or its derivatives suitable for relieving A-V block fall within the range of 0.1–20 mg/kg. The corresponding plasma level range desired is 0.2–40 $\mu$g/ml, preferably 0.9–20 $\mu$g/ml, and most preferably 6–10 $\mu$g/ml. Effective dosages of other antagonists of adenosine can be readily determined by monitoring the effect of a given dose on the P-R interval of a heart beat as measured by an electrocardiogram. An effective dose may be recognized by the alleviation of first, second or third degree heart block in the absence of complications.

Theophylline and its derivatives, particularly aminophylline, are well known in the treatment of bronchial asthma and are considered safe for human use. Standard procedures for administration of theophylline and aminophylline at effective dosage levels are well established and are well known to those skilled in the art. For example, the recommended therapeutic range for plasma levels of theophylline for patients with reversible obstruction of the airways is from 10 to 20 $\mu$g/ml. Similar plasma levels are suggested above for the treatment of A-V block. These plasma levels may be established by standard methods of administration, including but not limited to intravenous injection, oral ingestion via tablets, capsules, or liquids, suppository implantation, intramuscular injection, and inhalation. Any of those methods that are able to provide the proper plasma level are suitable for the present invention, but because the need for rapid onset of action by the antagonist in conditions of danger to heart tissue caused by an A-V block, intravenous injection is preferred. Intravenous administration of theophylline or a derivative may consist of a single injection, a loading dose followed by continuous administration of a lower level maintenance dose, injections spaced over a period of time, continuous injection of a low level maintenance dose, injections spaced over a period of time, continuous injection of a low level maintenance dose, or other types of administration that are suitable for the particular needs of the individual human or animal being treated. Dosages of theophylline or aminophylline required for specific plasma levels are well known to those in the art, as shown in the article "Rational Intravenous Doses of Aminophylline", by Mitenko and Ogilvie, New England J. Med., 289, pp. 600–603 (1973). For example, to achieve a theophylline plasma level of 10 $\mu$g/ml, theophylline is administered in an initial loading dose of 5–6 mg/kg followed by a continuous maintenance dose of 0.90 mg/kg/hr.

Administration of these amounts is sufficient for achieving and maintaining a plasma level of 10 $\mu$g/ml for any method in which theophylline or a derivative is absorbed into the blood stream without being destroyed. Examples, not intended to be limiting, include intravenous injection, absorption by the large intestine from suppositories, absorption by the small intestine from capsules that release theophylline or other methylxanthines in the intestine after passing through the stomach, or absorption through the lungs. Methods that require the methylxanthine to pass through the stomach may be subject to destruction of antagonist and accordingly must be either protected in a form that is not destroyed in the stomach or administered in a larger dose so that the amount reaching the blood stream is sufficient to achieve the desired effective level.

Other plasma levels may be achieved by using multiples or fractions of the doses disclosed above. If a derivative of theophylline is used, the dose of the derivative needed can be calculated by known methods. For example, aminophylline, which is theophylline ethylenediamine, contains about 80 mg of theophylline per 100 mg of aminophylline. Therefore, to achieve and maintain a theophylline plasma level of 10 $\mu$g/ml, aminophylline would be administered in an initial loading dose of 7.0 mg/kg followed by a continuous maintenance dose of 1.1 mg/kg.hr.

Antagonists of adenosine may be admixed with any pharmaceutically acceptable carrier or carriers, such as water, ethanol, inert solids, or any other carrier customarily used for the type of administration in question.

Antagonists of adenosine may be mixed with atropine or other drugs suitable for treating disorders of the heart to produce compositions of widely ranging uses. For example, a composition comprising both atropine and an antagonist of adenosine, such as theophylline or its derivatives, may be used to treat A-V conduction block caused by both vagus nerve disorders and hypoxia or ischemia. When the cause of A-V conduction block is not known, it may be desirable to administer such a composition of atropine and a theophylline derivative in order to immediately alleviate the symptoms of heart block without requiring separate injections to determine the actual cause of the block. Such a composition for intravenous injection might include atropine in the ranges 0.1–3 mg, preferably 0.3–1 mg and a derivative of theophylline equivalent to 0.1–20 mg/kg, preferably 0.45–10 mg/kg, and most preferably 3–5 mg/kg of theophylline.

Having generally described the invention, a more complete understanding can be obtained by reference to certain specific examples, which are provided herein for purposes of illustration only and are not intended to be limiting unless otherwise specified.

EXAMPLE 1

The similar effects of exogenous adenosine and of hypoxia on perfused rabbit and guinea pig hearts have been demonstrated. Impaired A-V conduction resulting from both of these conditions has been relieved by the administration of aminophylline.

Experiments were carried out using isolated, perfused rabbit and guinea pig hearts. Adult rabbits of either sex (New Zealand White), weighing 6-8 kg, were anesthetized with sodium pentobarbital (25 mg/kg,iv) whereas guinea pigs of either sex (Hartley) weighing 450-700 g, were stunned by a blow to the head. The hearts were removed rapidly and rinsed with ice cold Ringer's solution. Retrograde aortic perfusion at a constant flow (Gilson pump Minipuls-2) of 3-5 ml/min per g was initiated immediately. In all experiments the non-recirculating perfusion fluid was modified Krebs-Henseleit solution (pH 7.4) with the following composition (mM): NaCl, 121.4; KCl, 4.7; $CaC_2$ 2.5; $MgSO_4$, 1.25; $KH_2PO_4$, 1.18; $NaHCO_3$, 25; glucose, 11. The solutions were gassed with 95% $O_2$+5% $CO_2$ and the temperature was maintained at 34°±1° C.

Figure 3:
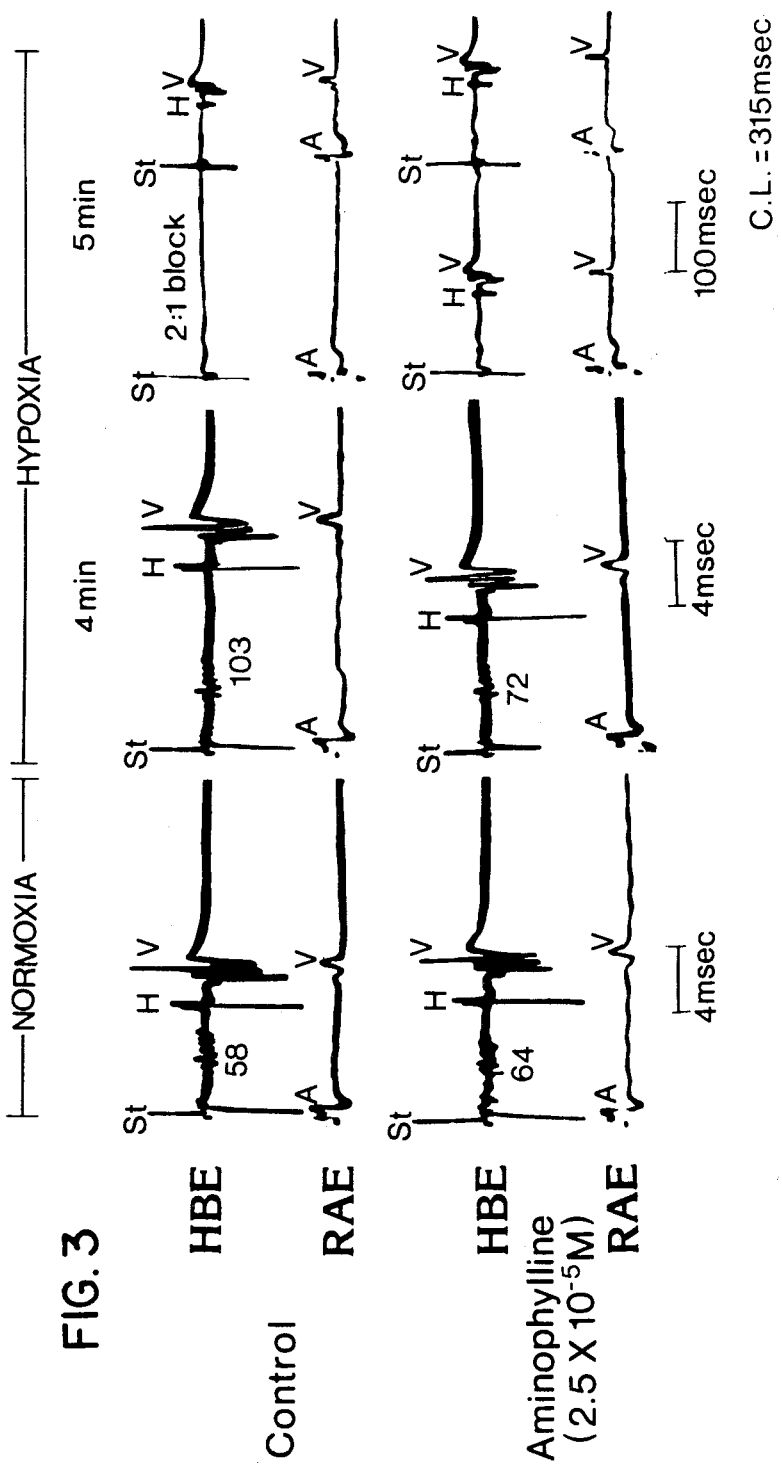

After the pericardium and other extraneous tissue had been removed, the right atrium was opened to expose the A-V node region. The sinoatrial node region also was excised. The heart was placed in a bath filled with Krebs-Henseleit solution and positioned in such a way that it was completely immersed. The right atrial wall was retracted with 6-0 nylon sutures to expose the region of the A-V node. The hearts were paced electrically at cycle lengths between 170 and 450 msec with a pair of Teflon-coated, silver wires placed on the upper surface of the right auricle. A physiological stimulator (Grass model S-4) provided the stimuli through a stimulus isolation unit as rectangular wave pulses of 2-3 msec duration and twice threshold intensity. Extracellular electrograms were recorded through bipolar, Teflon-coated, stainless steel wires (o.d., 0.0045") on the crista terminalis and left ventricle. The electrode for the the His bundle electrogram (HBE) consisted of a small (2-3 mm) stainless steel electrode (insulated except for the tip) soldered to a copper wire (o.d., 0.0031"), i.e., similar to a floating electrode. These electrodes had a resistance of 2-5 MΩ. We adjusted the position of the HBE electrode until a discernible spike from the bundle of His was recorded (as illustrated in FIGS. 2 and 3. The bipolar electrograms were obtained by connecting these two electrodes to a differential amplifier (Tektronix model 2A61). The signals from the right atrial electrogram (RAE) and HBE were amplified and displayed on a dual-beam oscilloscope (Tektronix model 502) and recorded on a strip-chart recorder (Gould-Brush model 220). Oscilloscope signals were displayed at sweep speeds of 10 to 50 msec/cm and photographed with a Kymographic camera (Grass). Strip chart recordings were obtained at a paper speed of 125 mm/sec.

On the right atrial and His bundles electrograms the stimulus artifact, the onsets of of atrial (A) and ventricular (V) depolarization and the His spike (H) were identified. From these features, the following measurements were taken: (1) cycle length, defined as the interstimulus interval; (2) A-H interval, which represents the conduction time from the atrial tissue to the bundle of His; (3) H-V interval, which represents the conduction time from the bundle of His to the ventricular tissue; and (4) A-V intervals, which represents the atrial to ventricular conduction time (A-VCT). The measurements are expressed in milliseconds.

After securing the electrodes 30 minutes passed before control measurements were begun. Control measurements preceded and followed all experimental interventions. When total A-V conduction time in the pre- and post-control differed by more than 10%, the intervening experimental data were discarded. Since A-V node conduction is very dependent upon cycle length, control and experimental measurements were made at similar cycle lengths. Furthermore, the effects of each experimental maneuver were observed at more than one cycle length.

Adenosine (Boehringer Mannheim or Sigma) was dissolved in perfusion medium and infused to achieve perfusion fluid concentraions of $10^{-7}$ to $10^{-4}$ M. Aminophylline (Invenex), acetylcholine (Sigma), atropine (Sigma), and manganese chloride (Mallinckrodt) were also dissolved in perfusion media and infused. To ensure complete mixing, all agents were introduced into the perfusion line, via a T-connection, before the peristaltic pump. All drug concentrations given herein are the calculated arterial perfusion fluid concentrations.

The experiments with hypoxia were performed only with guinea pig hearts. Hypoxia were produced by switching from perfusion fluid gassed with 95% $O_2$+5% $CO_2$ to perfusion fluid gassed with 95% $N_2$+5% $CO_2$ (pH 7.4; $PO_2$, 19-25 mm Hg). After a control (normoxic) period, hypoxic perfusion was effected for 5 minutes followed by reinstitution of normoxic perfusion. After 27 minutes of normoxic perfusion, infusion of aminiophylline was begun (final perfusion fluid concentration=2.5×$10^{-5}$ M). Three minutes later, a second 5-minute period of hypoxia was induced in the continued presence of aminophylline. This period of hypoxia was followed by a 30 minute perfusion with oxygenated perfusion fluid. Aminophylline was discontinued after 5 minutes of reoxygenation. Finally, another 5-minute period of hypoxic perfusion and a subsequent 30-minute normoxic perfusion were performed. A-H, H-V and A-V intervals were measured every half-minute.

In most cases, statistical analyses were based on the $\tau$-distribution for paired (experimental vs. average pre- and post-control) data. Linear regression analysis was used to evaluate the possible dependence of the percent increment in A-V conduction time upon cardiac cycle length for various doses of adenosine. One-way analysis of variance was used to evaluate the dependence of responses on adenosine dose (Snedecor and Chochran, Statistical Methods, ed. 6, chap. 10, Ames, Iowa, The Iowa State Univerisy Press, pp. 258-298 (1976)).

Figure 4:
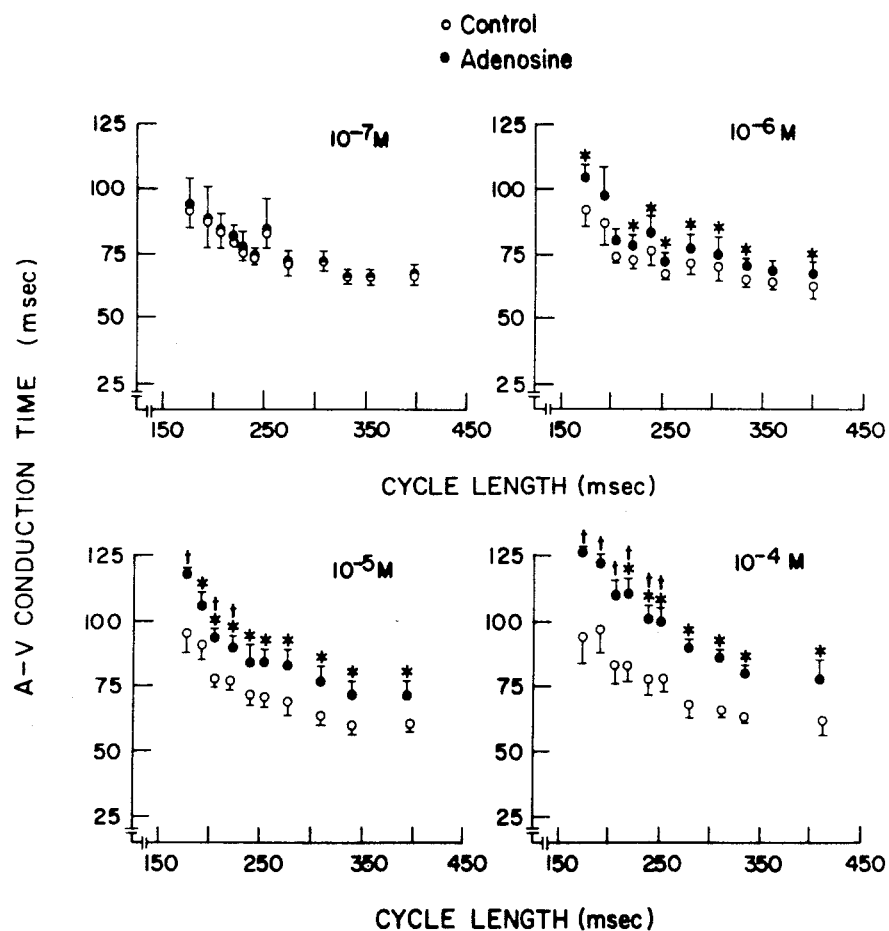
Figure 5:
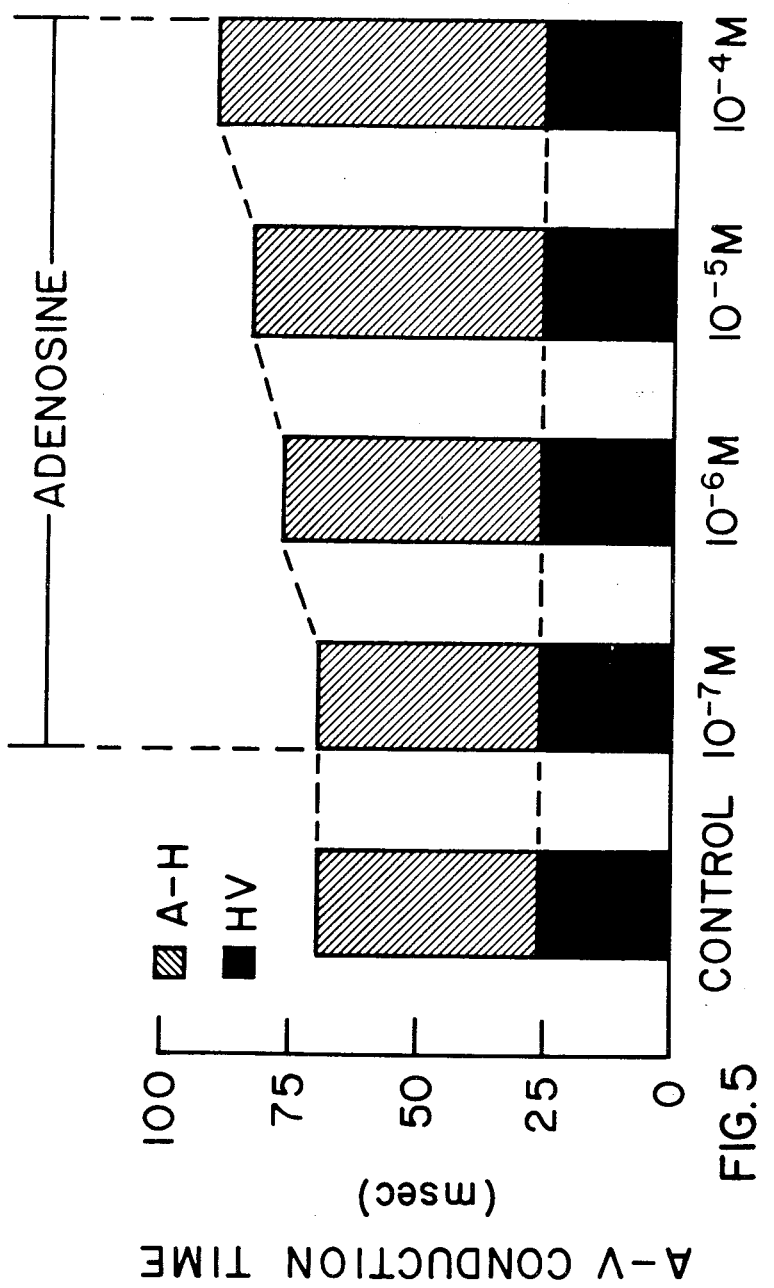

Adenosine prolonged A-V conduction time in isolated perfused rabbit hearts. In these experiments, displayed in FIGS. 4 and 5, the isolated heart preparation was paced at several different rates during a control (no infusion) period. Adenosine was then infused to achieve a perfusion fluid concentration of $10^{-7}$, $10^{-6}$, $10^{-5}$, or $10^{-4}$ M and the paced rates were repeated. Finally, a post-control series of measurements was made. As seen in FIG. 5, adenosine prolonged the A-H interval without changing the H-V interval. FIG. 4 summarizes the data from 20 rabbit heart preparations. No effect of adenosine was seen at $10^{-7}$ M, but the higher doses clearly prolonged the A-V conduction time. Statistical analysis was hampered somewhat by small numbers of replicated points at certain cycle lengths. The trend of the data was clear, however, as 150 of 155 trials at the three highest doses showed prolonged A-V conduction time with adenosine. Another statistical problem was caused by the tendency of $10^{-5}$ nd $10^{-4}$ M adenosine to cause second-degree heart block at the higher heart rates in some preparations (11 trials indicated by crosses in FIG. 5). Although this made quantification difficult, it clearly strengthens the conclusion that adenosine prolonges A-V conduction in isolated rabbit hearts.

FIG. 4 also demonstrates the tendency for A-V conduction time to increase with heart rate, i.e., as cycle length decreases. This is a well-known effect (Merideth et al., Circ. Res., 23, pp. 69–85 (1968)). The A-V conduction time was subdivided into its A-H and H-V intervals in 14 of the 20 rabbit hearts in this series (i.e., those in which a His electrogram was obtained). The H-V interval averaged $25\pm1$ msec for these hearts and showed no dependence on cycle length. Therefore, all the changes in A-V conduction time as a function of cycle length are accounted for by changes in the A-H interval. In addition to showing that the adenosine-induced changes in A-V conduction time were due solely to changes in the A-H interval, FIG. 5 also indicates a significant concentration-dependence of this adenosine effect. The percentage increments in A-V conduction time showed only very weak dependence on cycle length for any adenosine dose. Linear regression analysis of these percent increment values against cycle length yielded low $r^2$ values (0.05–0.46) and shallow slopes (1–3%) per 100 msec cycle length) for the groups of data for the three highest adenosine concentrations. Therefore, the values were pooled for each dose. Cases in which second-degree heart block was induced by adenosine were not included in these calculations, leading to some underestimation of the effects of the high adenosine concentrations. The lowest adenosine concentration ($10^{-7}$ M) caused a $1\pm1\%$ (mean$\pm$SEM, $\eta=23$ paired comparisons) increase in A-V conduction time. This was not significantly different from no effect. But, adenosine at $10^{-6}$ M caused an $8\pm1\%$ ($\eta=52$) increase in A-V conduction time; adenosine at $10^{-5}$ M caused a $21\pm2\%$ ($\eta=59$) increase; adenosine at $10^{-4}$ M caused a $31\pm2\%$ ($\beta=44$) increase. These values were all significantly different from zero and from each other [analysis of variance for one-way classification by adenosine dose].

Figure 6:
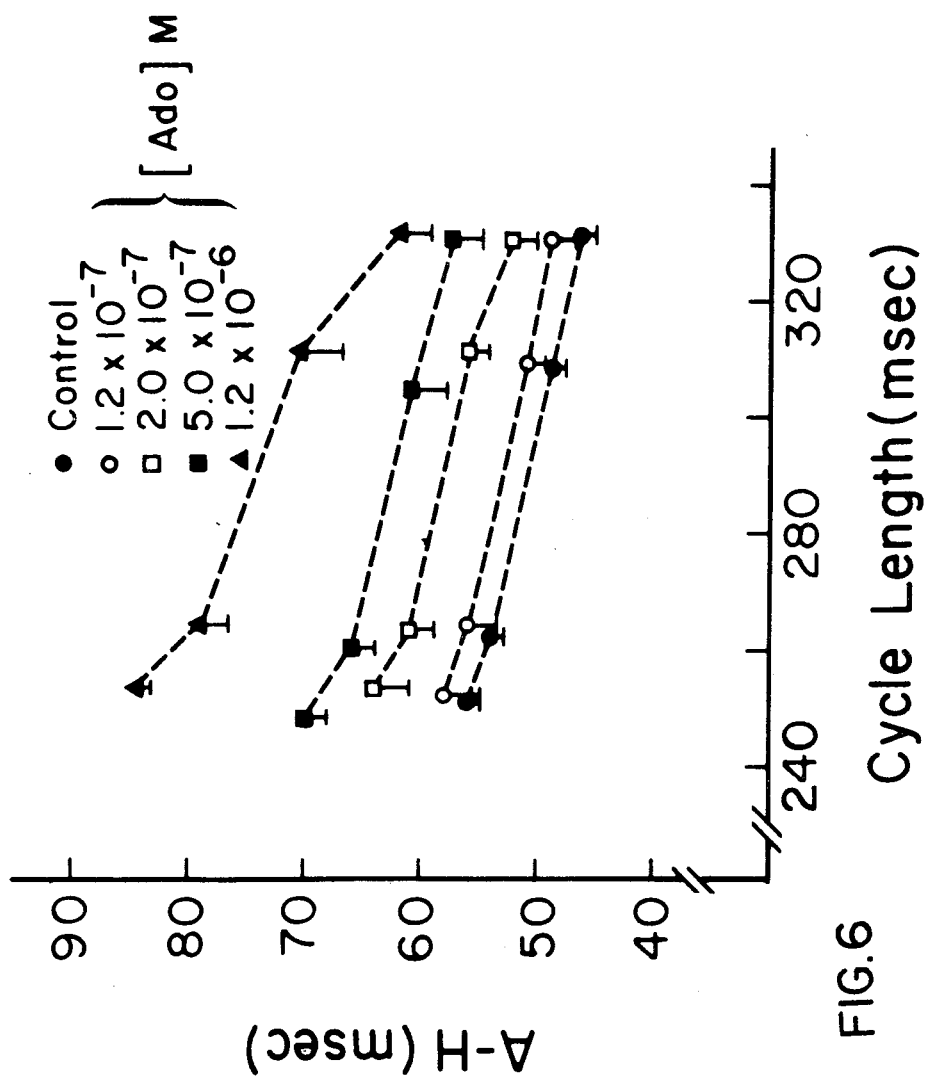

Adenosine also prolonged A-V conduction time and A-H interval in isolated, perfused guinea pig hearts (FIG. 6). A protocol similar to that used for rabbits hearts was followed. A-H and H-V intervals, as well as A-V conduction time, were measured for each preparation. The threshold for effects in the guinea pig was lower, with $1.2\times10^{-7}$ M adenosine causing a $4\pm$increase in A-V conduction time in this species ($\eta=20$ paired comparisons from five hearts, all cycle lengths, different from zero at $p<0.001$ level) compared to the statistically insignificant change of $1\pm1\%$ seen with $1.3\times10^{-7}$ M adenosine in the rabbit hearts. Furthermore, the dose-response relationship appeared to be much steeper in guinea pig hearts. Adenosine at $1.2\times10^{-6}$ M caused a $31\pm4\%$ ($\eta=9$ paired comparisons from four hearts, all cycle lengths) increase in A-V conduction time in this species as compared to only an $8\pm1\%$ increase at a similar concentration in rabbit hearts. Furthermore, adenosine at $5\times10^{-6}$ M produced second-dgree heart block in 17 of 17 trials with guinea pig hearts (cycle lengths=260–330 msec), and $1.2\times10^{-5}$ M adenosine produced complete A-V block (A-V dissocation) in each of eight guinea pig hearts (not shown). Comparable concentrations in rabbit hearts produced only relatively mild A-V conduction delay or, at most, occasional second-degree block at high heart rates (FIG. 4).

In the guinea pig heart, as in the rabbit heart (FIG. 5), both the effects of adenosine and the conduction changes with cycle length were confined to the A-H interval (FIG. 6), whereas the H-V interval remained unaltered at $14\pm1$ msec ($\eta=$the 7 hearts represented in FIG. 6). Conclusions about the relative threshold and dose response steepness for the two species are equally as valid for A-H interval as for A-V conduction time although, of course, the perecentage calculated are slightly higher for A-H intervals.

FIG. 2 shows an electrogram from an experiment in which $10^{-6}$ M adenosine induced second-degree heart block (4:3, panel B) in a guinea pig heart. Two minutes after the initiation of an aminophylline ($10^{-5}$ M) infusion (panel C), in the continued presence of adenosine, the heart block was eliminated and the A-H interval was only 16% greater than the control value (panel C vs. panel A).

Figure 7:
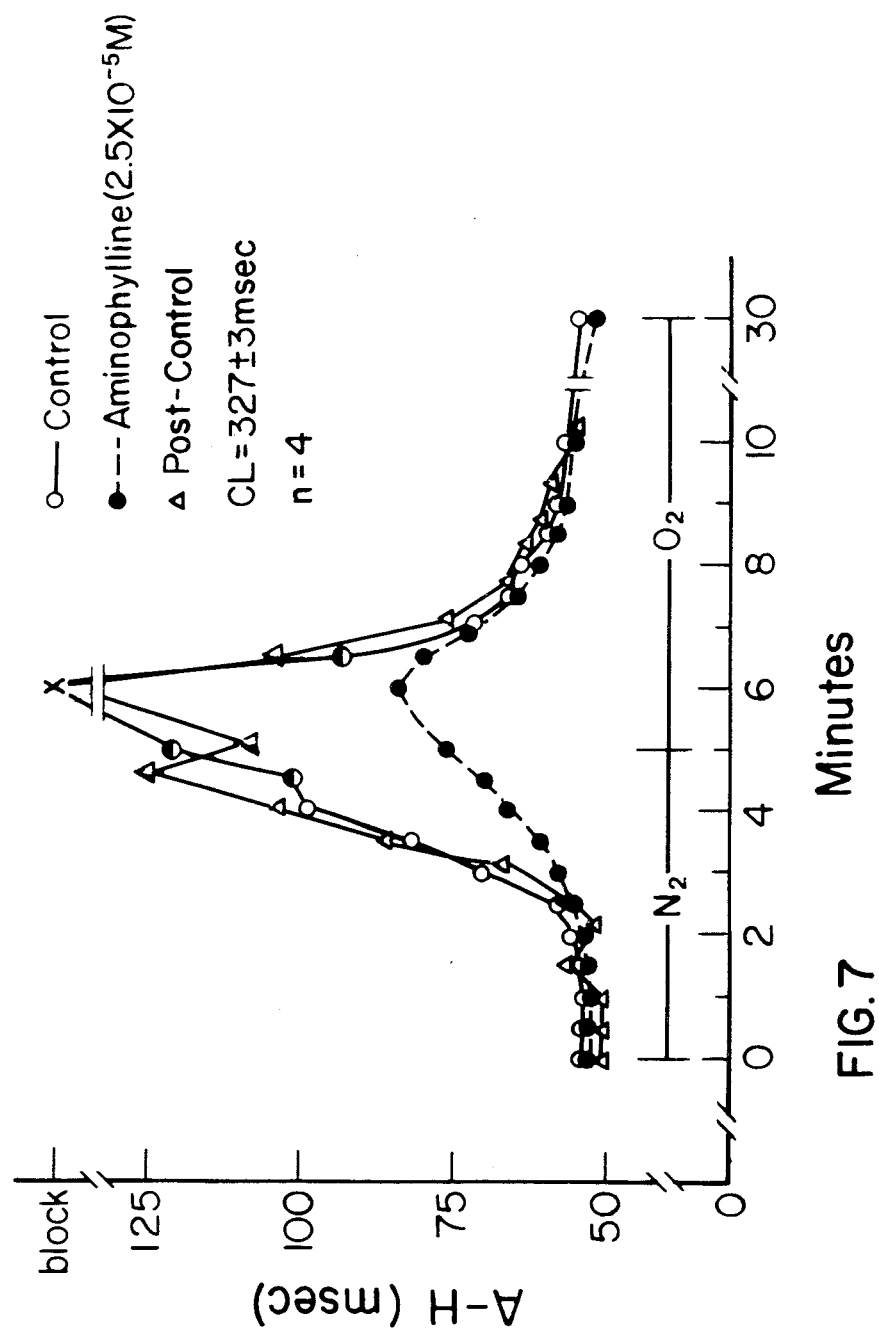

This pattern was seen in eight hearts at cycle lengths between 176 and 332 msec. In other experiments, for example the one summarized in Table 1, adenosine did not cause second-degree heart block at certain cycle lengths, but only prolonged the A-H and A-V intervals. In three experiments of this type, involving several different pacing rates, $10^{-5}$ M aminophylline reduced the $10^{-6}$ M adenosine-induced increment in A-H interval by 65–100%. Aminophylline by itself had not significant effect on A-V conduction (FIGS. 3 and 7).

TABLE 1

Effects of Aminophylline and Atropine on the A-H Interval of Guinea Pig Hearts in the Presence of Acetylcholine, Adenosine, and $MnCl_2$

| Agonist | Cycle Length (msec) | A-H (msec) Control | Agonist | Agonist + aminophylline ($2.5 \times 10^{-5}$ M) | Agonist + atropine ($10^{-6}$ M) |
|---|---|---|---|---|---|
| Acetylcholine | 376 | 52 | 64 | 63 | 52 |
| ($6.2 \times 10^{-8}$ M) | 328 | 60 | 66 | 66 | 58 |
| | 288 | 63 | 82 | 84 | 64 |
| | 264 | 74 | 5:4 Block | 5:4 Block | 72 |
| Adenosine | 376 | 52 | 63 | 55 | 62 |
| ($1.2 \times 10^{-6}$ M) | 328 | 58 | 68 | 56 | 69 |
| | 288 | 64 | 78 | 64 | 78 |
| | 264 | 72 | 5:4 Block | 74 | 5:4 Block |
| $MnCl_2$ | 376 | 48 | 70 | 74 | |
| ($2 \times 10^{-4}$ M) | 328 | 54 | 88 | 89 | |
| | 288 | 60 | 100 | 100 | |

TABLE 1-continued

Effects of Aminophylline and Atropine on the A-H Interval of Guinea Pig Hearts in the Presence of Acetylcholine, Adenosine, and MnCl$_2$

| Agonist | Cycle Length (msec) | A-H (msec) | | | |
|---|---|---|---|---|---|
| | | Control | Agonist | Agonist + aminophylline (2.5 × 10$^{-5}$ M) | Agonist + atropine (10$^{-6}$ M) |
| | 264 | 68 | 3.2 Block | 2.1 Block | |

Aminophylline's antagonistic action appears to be relatively specific for adenosine. Acetylcholine and manganese chloride were administered as infusions to several gunea pig heart preparations. The concentrations of these agents were adjusted to achieve A-H interval prolongation similar in magnitude to that caused by adenosine at comparable pace rates (Table 1, one experiment shown). Aminophylline (2×10$^{-5}$ M) blocked or greatly attenuated the adenosine responses, as already discussed, but was without effect on the responses to acetylcholine or manganese chloride. Atropine (10$^{-6}$ M), however, eliminated the effects of acetylcholine while exerting no apparent antagonism against adenosine. Qualitatively similar effects of atropine and aminophylline on responses induced by adenosine, acetylcholine, and manganese chloride were obtained from a total of three preparations.

Hypoxia was induced in guinea pig heart preparations by switching from an oxygenated to an hypoxic perfusion fluid. As shown in the top panels of FIG. 3, the A-H interval was prolonged and second-degree heart block eventually ensued. There was no measurable significant change in the H-V interval. Aminophylline, at a concentration (2.5×10$^{-5}$ M) which sharply attenuated the A-V nodal conduction effects of adenosine (FIG. 2; Table 1), also decreased the prolongation of conduction induced by hypoxia (FIG. 3, bottom panels). These experiments are summarized in FIG. 7. Two control runs, consisting of 5 minutes of hypoxic perfusion, were sandwiched around an hypoxic perfusion in the presence of 2.5×10$^{-5}$ aminophylline. Thirty minutes of normoxic perfusion intervened between hypoxic periods. Note in FIG. 7, summarizing those experiments performed at a pace rate of ~3 Hz, that recovery was complete after each hypoxic period and that the initial A-H intervals were approximately equal in all three runs. The first effects of hypoxia on the A-H intervals were noticed about 2.5–3 minutes after perfusates were changed. The minimal transit time of our system, as measured by appearance of trypan blue at the aortic cannula tip after switching from a colorless to a trypan blue-containing perfusion fluid, was ~1.5 minutes. The trypan blue concentration at the cannula tip reached a plateau at ~3.2 minutes after the change of perfusion fluids. Therefore, much of the delay in onset of the effects of hypoxia can be attributed to the delay in onset of the hypoxic stimulus. Beyond these first minutes, the progressive effect of the A-V conduction defect can be attributed to the progressive effect of hypoxia itself. The effects progressed for the first 1-2 minutes of the recovery period due to the delayed arrival of the normoxic solution through the perfusion system.

Although this is obviously a non-steady state, the time course of the A-V conduction defect was reproducible (compare pre- and post-control curves in FIG. 7). It is also obvious that aminophylline diminished the A-H interval increment at any point during hypoxia. Statistical analysis was hampered by the appearance of second-degree heart block in some (half-filled symbols or "x") of the preparation during the control hypoxic periods. Second-degree heart block never appeared during the 5-minute hypoxic periods in the presence of aminophylline, however, although one preparation developed block during the early moments of the recovery period. Furthermore, in every case in which the control runs showed a simple A-H prolongation, the aminophylline run showed a shorter A-H interval than either of the surrounding controls. Using just those cases in which aminophylline merely diminished an A-H interval prolongation, (i.e., ignoring the cases where second-degree heart block occurred), we calculate that the hypoxia-induced changes in A-H interval were attenuated 78% by aminophylline.

The A-V conduction defects appeared to be more severe in those experiments with a pace rate of ~4 Hz (not shown) than those in with the lower pace rate of ~3 Hz. The appearance of second-degree block was more common and occurred sooner with the higher rate. In some cases, the post-control run displayed some deterioration of the preparation, as noted by an imcomplete recovery. Nonetheless, the same pattern of amelioration by aminophylline was observed.

The results presented here confirm previous observations (Drury and Szent-Gyorgyi, J.Physiol. (Lond.), 68, pp 213–237 (1929); Stafford, Br.J. Pharmacol. Chemothery 28, pp 218–227 (1966); and Schrader et al., Pfiuegers Arch, 372, pp 29–35 (1977)) that adenosine induces A-V node conduction delay and block. An additional finding is that the effects of adenosine on A-V node conduction are due to increased conduction delay between the atria and His bundle, i.e., an increased A-H interval. In contrast, the H-V interval is not affected by adenosine even at high concentrations (10$^{-4}$ M). These new findings are consistent with the idea that adenosine depresses slow channel-mediated action potentials (atria and/or A-V node) whereas fast channel-mediated action potentials are not affected. (Schrader et al., J.Mol. Cell. Cardiol., 7, pp. 427–433 (1975); Belardinelli et al., Pfluegers Arch., 380, pp. 19–27 (1979)). The selectivity of adenosine's action on the A-V node is similar to that of other slow-channel blockers, such as MnCl$_2$ and varapamil (Benitez et al., Pfluegers Arch., 345, pp 61–72 (1973); Zipes and Mendez, Circ. Res., 32, pp 447–454 (1973). In comparison to the effects of MnCl$_2$ and verapamil (Kohlhardt et al., Pfleugers Arch., 33, pp 115–123 (1973), however, the effects of adenosine have a rapid onset (<1 min) and can be reversed rapidly on washout.

Guinea pig hearts were more sensitive to be effects on adenosine than rabbit hearts, i.e., the threshold dose was lower and A-V block was seen more frequently in guinea pig hearts. Species differences with respect to sensitivity to the effects of adenosine on A-V node conduction have been reported previously (Drury and Szent-Gyorgyi, see above). The basis for these differences is not understood.

Temperature can modify the action of adenosine on A-V conduction. Drury and Szent Gyorgyi noted a decreased sensitivity of the guinea pig heart (induction of A-V block) to adenosine at higher temperatures. Pilot experiments at 37° C. also showed a right-shifted adenosine dose-response curve compared to the data presented here, obtained at 34° C. The lower temperature was chosen because of the superior preparation stability it provided. Even at 37°, however, complete A-V block in the guinea pig heart with $10^{-4}$ M adenosine (three experiments) was obtained. As noted below, hypoxic myocardial adenosine levels can approach this concentration. Therefore, the basic conclusion is not altered because of use the of a low temperature.

In this study the A-H interval prolongation induced by adenosine was blocked by $10^{-5}$ M aminophylline, and this antagonism was specific, inasmuch as similar acetylochline- and $MnCl_2$-induced effects were not blocked by aminophylline. These findings are consistent with the notion that adenosine is competitively inhibited by theoplylline (Bunger et al., Pfluegers Arch., 358, pp. 213-224 (1975)) and probably affects the A-V node conduction system by acting on the plasma membrane, as has been demonstrated for other tissues using adenosine that had been complexed to high molecular weight substances (Olsson et al., Circ. Res., 39, pp. 93-98 (1976); Shrader et al, Pfluegers Arch., 372, pp. 29-35 (1977); Hartzell, J. Physiol. (Lond.), 293, pp. 23-49 (1979)).

EXAMPLE 2

Aminophylline (3-5 mg/kg) was administered to each of two patients suffering from acute myocardial infarction. Each patient had developed second degree A-V node block of the "Wenckebach" type. Administration of the aminophylline rapidly restored A-V conduction and abolished the A-V block.

Patients with Myocardial Infarct and A-V Heart Block
Patient #1: Female, 52 years old—80 kg—Posterior Myocardial Infarction (M.I.)

8 hours after onset of the symptoms of myocardial infarction a first degree block was observed.

Aminophylline (3 mg/kg) was administered during a 10 min. period.

Normal A-V conduction was restored.

Electrocardiograms for patient #1 are shown in FIG. 8.

Patient #2: Male, 64 years old—72 kg—Posterior Myocardial Infarction (M.I.)

24 hours after onset of the symptoms of myocardial infarction the patient developed a second degree A-V block (varying from 2:1, 3:2, 4:3 A-V block).

Aminophylline (3 mg/kg) was administered during a 10 min. period. One-to-one A-V conduction was resumed. Second degree A-V block recurred after aminophylline washout.

48 hours after the initial M.I., Aminophylline was administered again, first as a loading dose (3 mg/kg) followed by a maintenance does of 0.45 mg/kg/hr.

After administration of aminophylline, 1-to-1 conduction resumed and continued as long as aminophylline was being infused.

Figure 10:
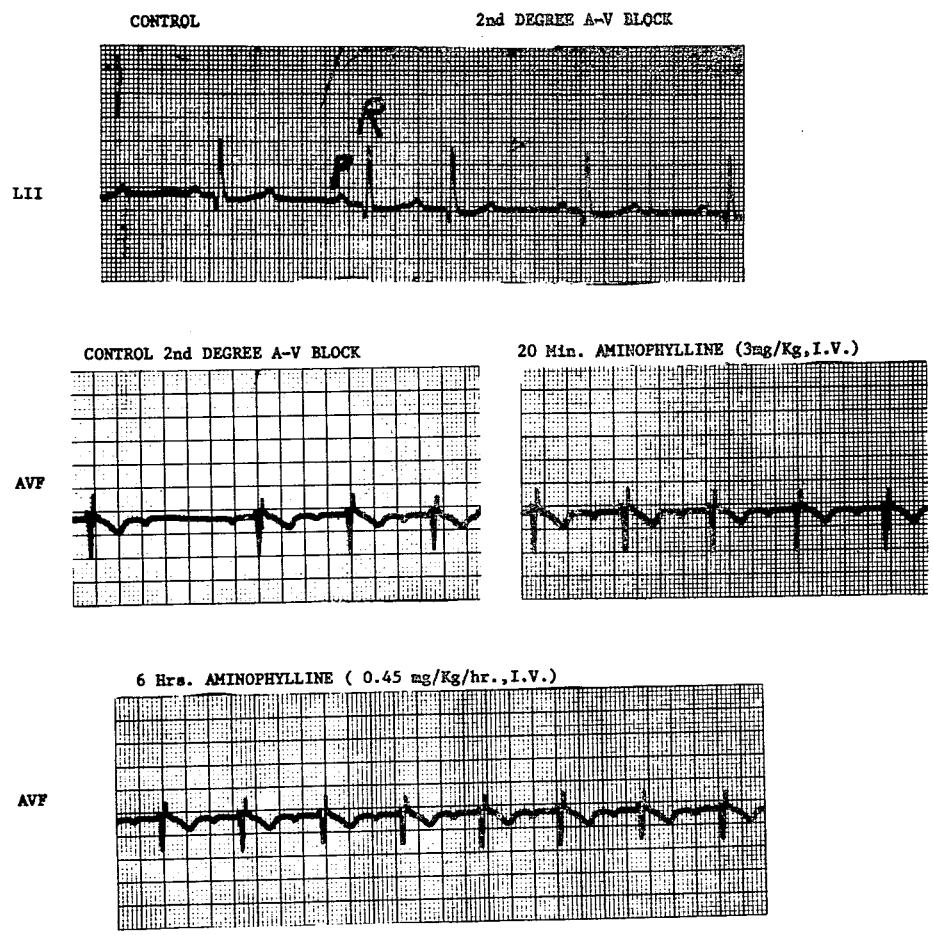
Figure 11:
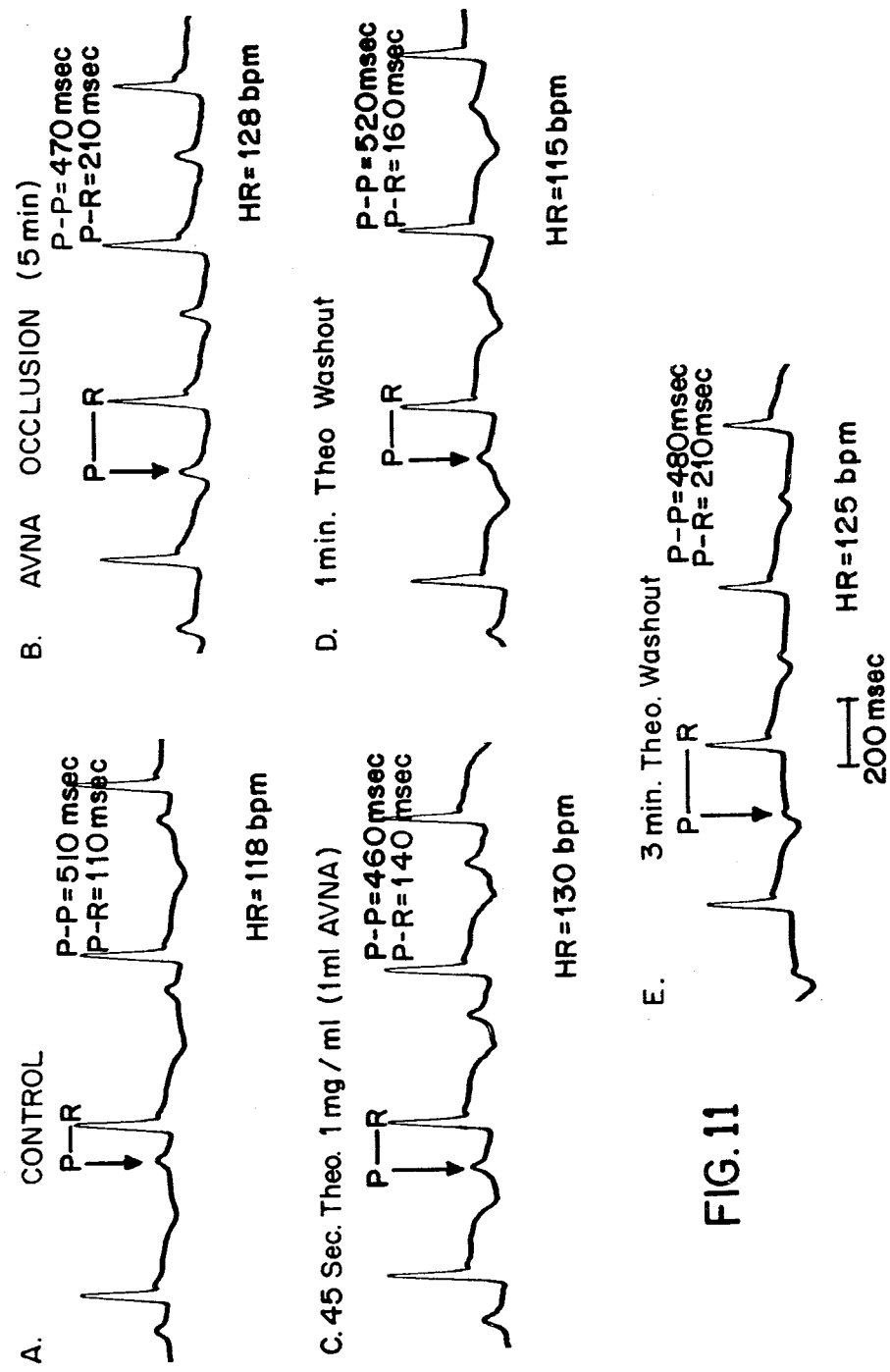
Figure 12:
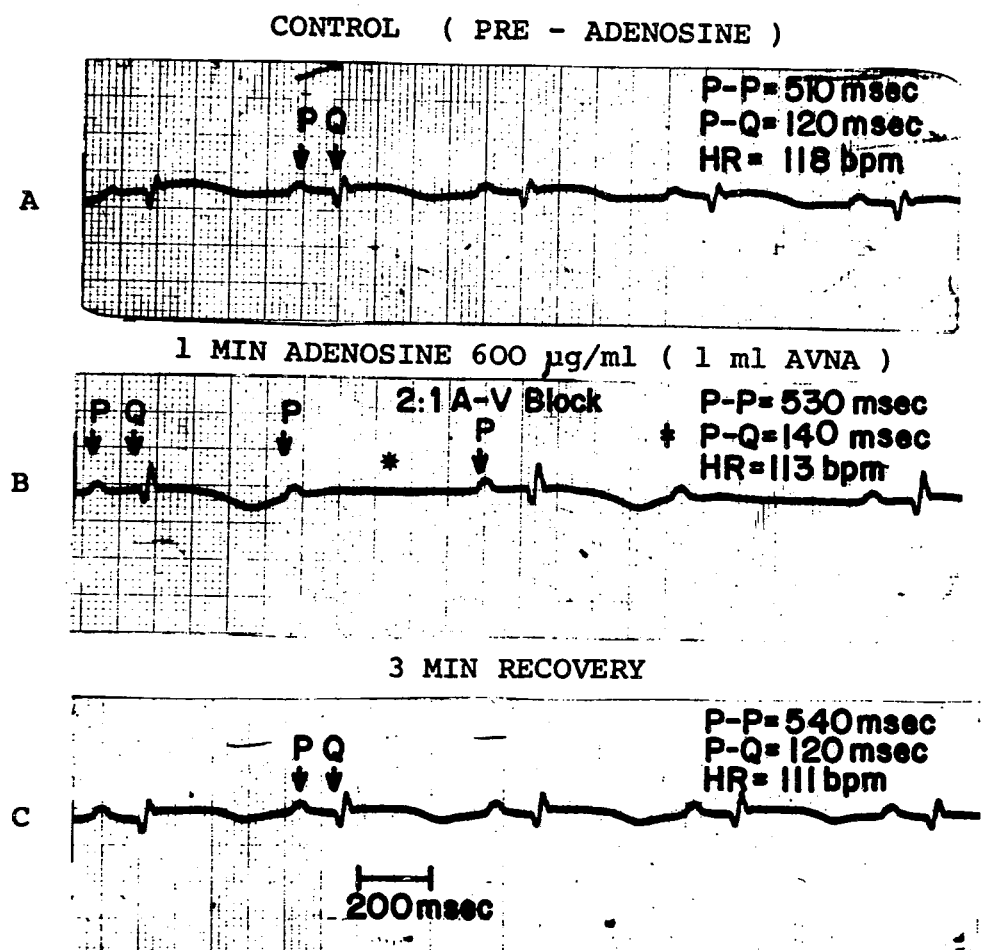
Figure 13:
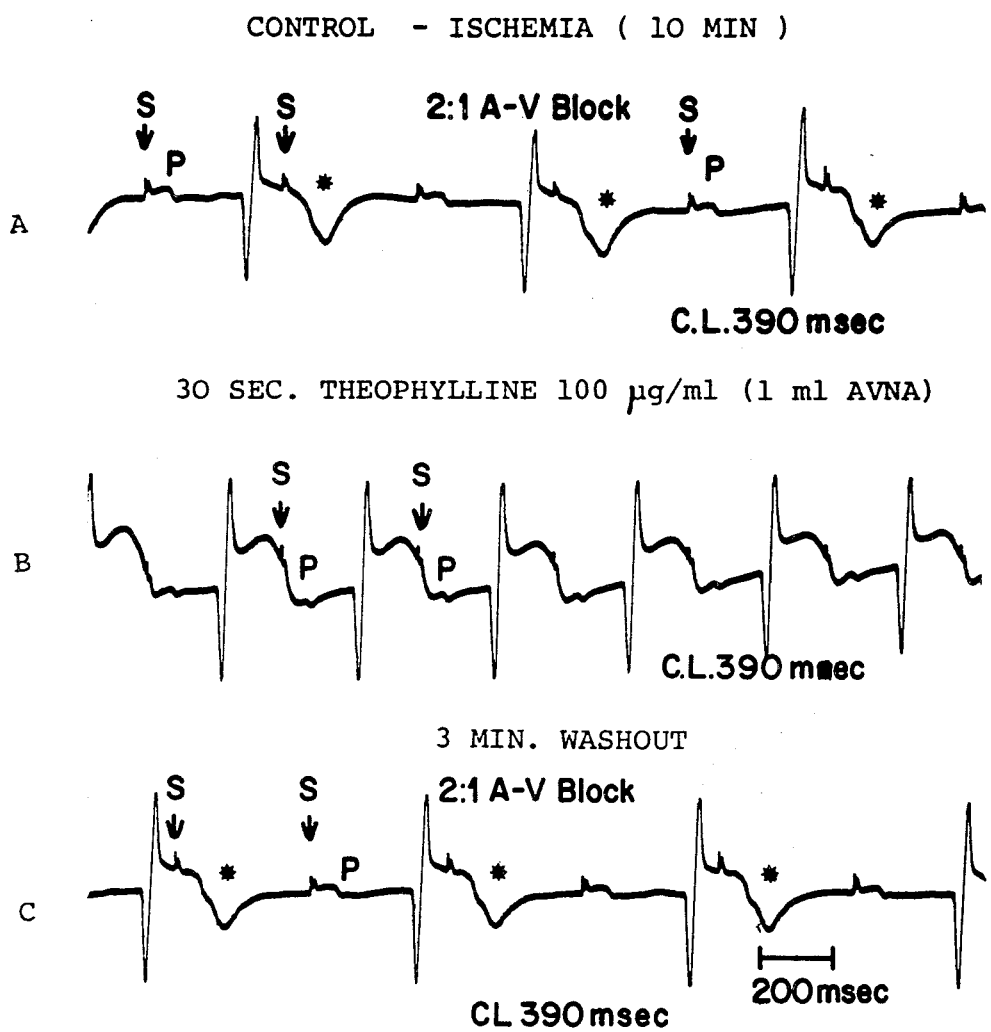
Figure 14:
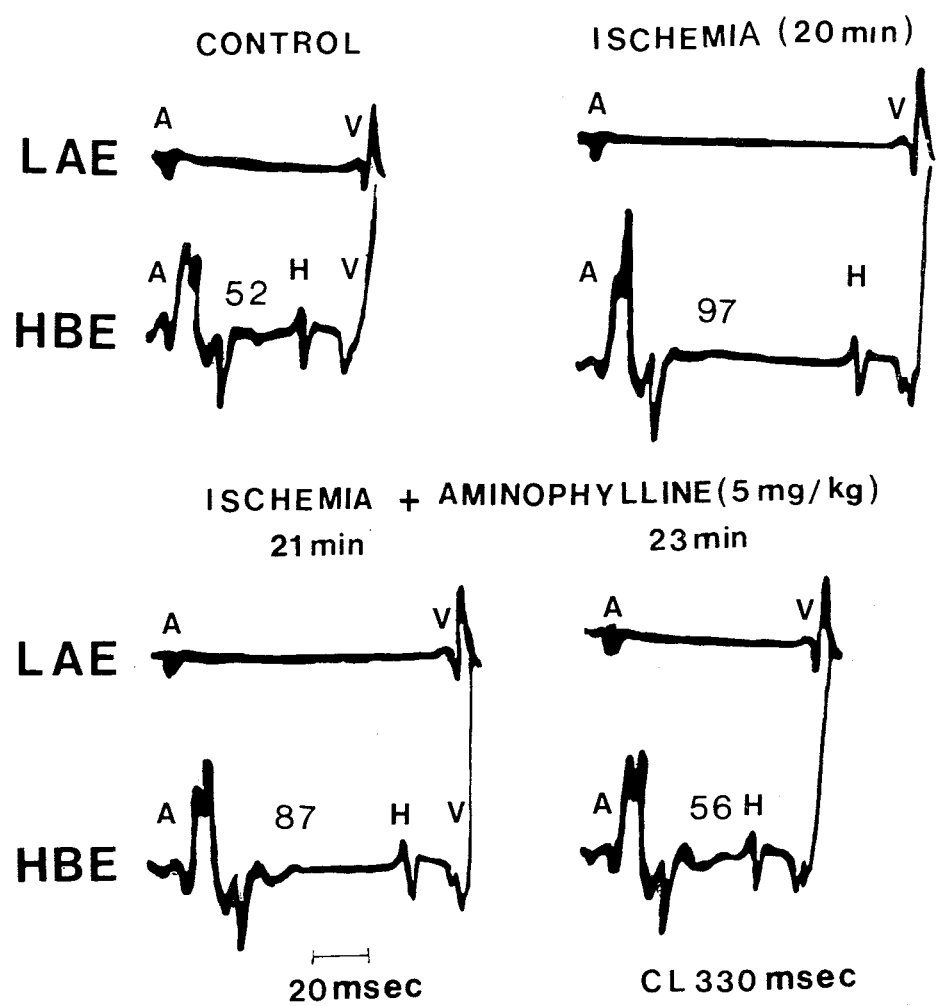
Figure 15:
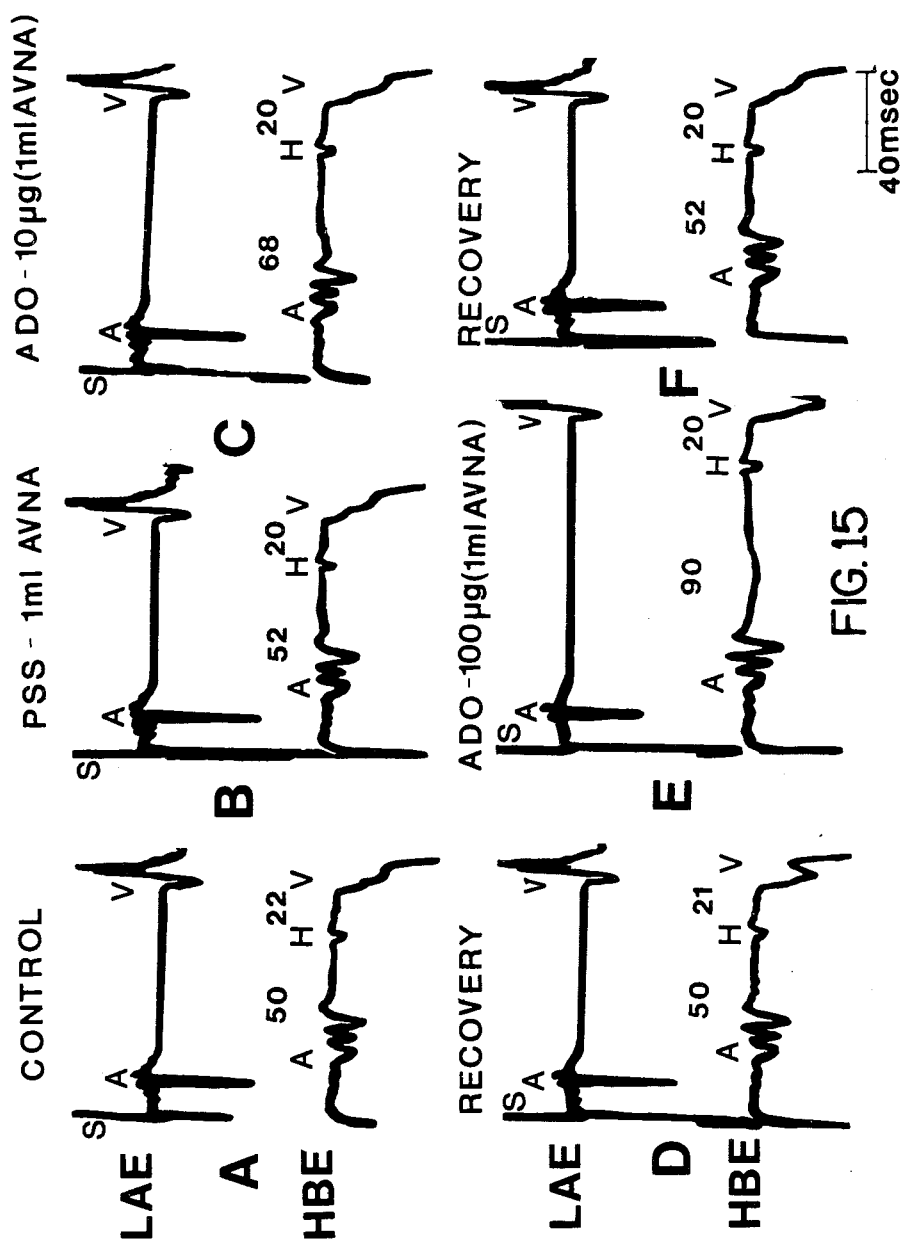

Electrocardiograms for patient #2 are shown in FIGS. 9 and 10.

It should be noted that these two patients received aminophylline 8 hours or more after the onset of myocardial infarction symptons. Interestingly enough, Adgey reported (see above) that only 1 of 11 patients seen 8 hours after M.I. responded to atropine, whereas 50% of the patients that were treated with atropine within 8 hours of the onset of M.I. symptoms responded favorably to the drug.

EXAMPLE 3

The effects of exogenous adenosine and of hypoxia on the heart of living dogs have been demonstrated. Impaired A-V conduction resulting from both of these conditions has been relieved by the administration of aminophylline.

Twenty-two mongrel dogs of either sex weighing 10-18 kg were anesthetized with sodium pentobarbital (30 mg/kg intravenously). Normal saline solution was administered throughout the experiment (10 ml/kg per hour) via a catheter in the left jugular vein. Arterial blood pressure was continuously recorded on a strip-chart recorder (Gould-Brush 2200) from a catheter positioned in the aorta via the right fermoral artery. Under controlled ventilation a left thoracotomy at the fourth intercostal space was performed and the heart exposed by pericardiotomy. For selective perfusion of the atrioventricular (A-V) node region the technique developed by James et al. J. Lab Clin. Med 76:240, 1970 was used. In brief, the atrioventricular node artery (AVNA), distal branch of the left circumflex, was carefully dissected. Sutures were placed around it, but the vessel was not cannulated until control measurements were taken. The AVNA was cannulated with a small polyethylene catheter and a continuous microdrip of physiological salt solution was given to keep the catheter open.

Electrical pacing at cycle lengths ranging from 450 msec to 250 msec was applied to the atrium through teflon coated stainless steel wires sutured to the left atrial appendage. The electrical stimulation was delivered from a Grass stimulator (Model 544) via a stimulus isolation unit (SIU) as rectangular wave pulses of 2-3 msec duration and twice threshold intensity.

A His-bundle electrogram was obtained with either a standard pacing or tri-polar electrode catheter (SF) having a 1 cm interelectrode distance. The electrode catheter was introduced into the aorta via the left carotid artery and then, advanced under manual control into the ascending aorta and finally wedged in the non-coronary cusp of the aortic valve. Its position was confirmed at the end of the experiment. Extracellular electrograms from atrium and ventricle were obtained with plunge electrodes, i.e., telfon coated stainless steel wires (0.0045 inch diameter) inserted into the left atrial appendage and left ventricle with use of 25 gauge hypodermic needles. A lead-II electrocardiogram was continuously monitored and recorded at a paper speed of 50 mm/sec. His-bundle, atrial and ventricular electrograms were obtained by connecting the electrode terminals to a differential amplifier (Tektronix model 5A222N). The signals were amplified and displayed on a dual-beam oscilloscope (Tektronix model 5440). Both His-bundle and left atrial and ventricular electrograms were filtered with a low cutoff of 80 Hz and a high cutoff of 1 $KH_z$. Oscilloscope signals were displayed at sweep speeds of 10 to 50 msec/cm and photographed with a Kymographic camera (Glass model C4).

In all experiments post-mortem coronary angiograms were performed to verify the anatomy of the cannulated AVNA.

On the left atrial, ventricle and His-bundle electrograms the stimulus artifact(s), the onset of atrial (A) and ventricular (V) depolarization, and the His spike (H) were identified. These features allowed us to measure: (1) Cycle length (C.L.) as the interstimulus interval; (2) A-H interval, which represents the atrial-to-His-bundle conduction time; (3) H-V interval, which represents the His-bundle-to-ventricular conduction time; and (4) A-V interval, which represents the atrial-to-ventricular conduction time (A-VCT).

In the lead-II electrocardiogram the atrial depolarization (P wave) and ventricular depolarization (QRS) were identified. The intervals P-R or P-Q which represent the conduction time from the atrium to the ventricle were measured. All the measurements are expressed in milliseconds.

Before cannulation of the atrioventricular node artery (AVNA), control recordings were made during left atrial pacing at cycle lengths varying from 450 msec to 250 msec. At 5 minutes after cannulation of the AVNA, new control recordings at the same pacing rates were obtained. Control measurements preceded and followed all experimental interventions involving injection of adenosine and any other drug to the AVNA. Whenever total A-V conduction time in the pre- and post-control differed by more than 10%, the intervening experimental data were discarded. Often the effects of the experimental interventions were observed at more than one cycle length.

Adenosine (Sigma) was dissolved in physiological salt solution to achieve concentration of 10 $\mu$g, 100 $\mu$g and 1000 $\mu$g per milliliter. Aliquots of 1-2 ml of these stock solutions were directly infused into the AVNA. Theophylline (Sigma) and atropine (Sigma) were also prepared in physiological salt solution to achieve the desired concentrations, and then infused into the AVNA. Between all interventions the AVNA was continuously perfused with physiological salt solution to assure complete washout of the infused drugs and keep the artery open. Aminophylline (Invenex) and dipyridamole (Persantin) were administered systemically (intravenously).

Electrocardiograms from these procedures are shown in FIGS. 11–15.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method of treating atrioventricular conduction block, comprising the steps of:
   administering to a human or animal with an atrioventricular conduction block an amount of an antagonist of adenosine sufficient to alleviate atrioventricular conduction block, wherein said antagonist competitively inhibits adenosine or reduces the level of adenosine present in myocardial tissue and associated fluids.

2. A method of treating atrioventricular conduction block according to claim 1, wherein said antagonist is a methylxanthine.

3. A method of treating atrioventricular conduction block according to claim 2, wherein said methylxanthine is administered in a dosage of 0.1–20 mg/kg.

4. A method of treating atrioventricular conduction block according to claim 2, wherein said methylxanthine is administered in a dosage of 0.45–10 mg/kg.

5. A method of treating atrioventricular conduction block according to claim 2, wherein said methylxanthine is administered in a dosage of 3–5 mg/kg.

6. A method of treating atrioventricular conduction block according to claims 2, 3, 4, or 5, wherein said methyl xanthine is theophylline or a derivative thereof.

7. A method of treating atrioventricular conduction block according to claim 6, wherein said administration is by intravenous injection.

8. A method of treating atrioventricular conduction block according to claim 6, wherein said administration is by oral ingestion.

9. A method of treating atrioventricular conduction block according to claim 6, wherein said administration is by insertion of a suppository.

10. A method of treating atrioventricular conduction block according to claim 6, wherein said theophylline derivative is aminophylline.

11. A method of treating atrioventricular conduction block according to claim 10, wherein said administration is by intraveneous injection.

12. A method of treating atrioventricular conduction block according to claim 10, wherein said administration is by oral ingestion.

13. A method of treating atrioventricular conduction block according to claim 10, wherein said administration is by insertion of a suppository.

14. A method of treating atrioventricular conduction block according to claim 2, wherein said administration is a continuous intraveneous injection.

15. A method of treating atrioventricular conduction block according to claim 14, wherein said continuous intravenous injection is at a rate of about 0.45 mg/kg/hr.

16. A method of treating atrioventricular conduction intravenous according to claims 14 o4 15, wherein said methylxanthine is theophylline or a derivative thereof.

17. A method of treating atrioventricular conduction block according to claim 16, wherein said theophylline derivative is aminophylline.

18. A method of treating atrioventricular conduction block according to claim 1, wherein said administration occurs concurrently with administration of atropine.

19. A method of treating atrioventricular conduction block according to claim 6, wherein said administration occurs concurrently with administration of atropine.

20. A method of treating atrioventricular conduction block according to claim 10, wherein said administration occurs concurrently with administration of atropine.

21. A method of treating atrioventricular conduction block according to claim 20, wherein 0.1–3 mg of said atropine is administered.

22. A method of diagnosing atrioventricular conduction block, comprising the steps of:
   administering an antagonist of adenosine to a human or other animal, wherein said antagonist competitively inhibits adenosine or reduces the levels of adenosine present in myocardial tissue and associated fluids; and
   monitoring the delay between atrial and ventricular contraction.

23. A method of diagnosing atrioventricular conduction block according to claim 22, wherein said monitoring is by electrocardiography.

24. A method of diagnosing atrioventricular conduction block according to claim 23, wherein said antagonist is a methylxanthine.

25. A method of diagnosing atrioventricular conduction block according to claim 24, wherein said methylxanthine is theophylline or a derivative thereof.

26. A method of diagnosing atrioventricular conduction block according to claim 25, wherein said theophylline derivative is aminophylline.

27. A method of diagnosing atrioventricular conduction block according to claims 23, 24, 25 or 26, wherein said administration is by intravenous injection.

* * * * *